United States Patent [19]

Koerwer

[11] 4,334,913

[45] Jun. 15, 1982

[54] SUBSTITUTED 3-HYDROXY-2-CYCLOHEXENE-1-ONE COMPOUNDS AS SUGAR ENHANCERS FOR PLANTS

[75] Inventor: John F. Koerwer, Perkasie, Pa.

[73] Assignee: Union Carbide Corporation, Danbury, Conn.

[21] Appl. No.: 249,649

[22] Filed: Mar. 31, 1981

[51] Int. Cl.$^3$ ............................................. A01N 31/04
[52] U.S. Cl. ............................................. 71/98; 71/76
[58] Field of Search ..................... 71/98, 121, 106, 76

[56] References Cited

U.S. PATENT DOCUMENTS 4,209,532  6/1980  Wheeler .............................. 424/331

FOREIGN PATENT DOCUMENTS

78/2404  4/1978  South Africa .

OTHER PUBLICATIONS

R. H. Hall and B. K. Lowe, J. Chem. Soc. 1949 (p. 2723).

*Primary Examiner*—Catherine L. Mills
*Attorney, Agent, or Firm*—William R. Moran

[57] ABSTRACT

A method for increasing the sugar content of plants by applying to such plants an effective amount of a substituted 3-hydroxy-2-cyclohexene-1-one.

33 Claims, No Drawings

SUBSTITUTED 3-HYDROXY-2-CYCLOHEXENE-1-ONE COMPOUNDS AS SUGAR ENHANCERS FOR PLANTS

FIELD OF THE INVENTION

This invention relates to a novel method for increasing the sugar content of plants by applying to such plants an effective amount of a 2-alkoxyiminoalkyl-5-alkylthioalkyl-3-hydroxy-2-cyclohexene-1-one or derivative thereof.

BACKGROUND OF THE INVENTION

Certain 1,3-cyclohexanedione compounds are known in the art. For example, U.S. Pat. No. 4,209,532 which issued June 24, 1980 discloses 2-aryl-1,3-cyclohexanedione compounds and alkali metal and ammonium salts thereof as being useful as miticide, mite ovicides, post-emergent herbicides and pre-emergent herbicides. In addition copending U.S. application Ser. No. 163,632 filed June 27, 1980 and assigned to the same assignee as this invention discloses 2-aryl-1,3-cyclohexanedione enol ester compounds as being useful to increase the sugar content of plants such as sugar cane (Saccharum officinerum) or sorghum (Sorghum vulgare). Increased sugar content, of course, increases the value of such plant.

SUMMARY OF THE INVENTION

In accordance with the present invention, it has now been discovered that certain 2-alkoxyiminoalkyl-5-alkylthioalkyl-3-hydroxy-2-cyclohexene-1-ones can be employed to increase the sugar content of plants when applied to such plants from 1 to 7 weeks prior to harvesting in an amount insufficient to exert a herbicidal effect. As a result, an earlier accumulation and significant increase in the sugar content of plants such as sugarcane (Saccharum officinerum) and sorghum (Sorghum vulgare) can be effected. The resulting plants are of greater value, of course, than the untreated plants.

DETAILED DESCRIPTION OF THE INVENTION

The 2-alkoxyiminoalkyl-5-alkylthioalkyl-3-hydroxy-2-cyclohexene-1-ones useful as plant sugar enhancers according to the present invention can be represented by the formula:

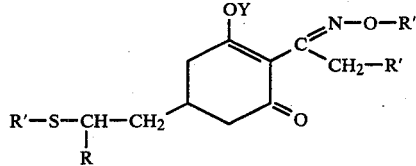

wherein:
R is an alkyl group having from 1 to 4 carbon atoms,
R' is an alkyl group having from 2 to 4 carbon atoms, and
Y is a hydrogen atom or an alkanoyl, alkenoyl or aryloyl group having up to 12 carbon atoms or a cation.

When R' is an alkyl group in the above formula, it can be either straight or branched chain, e.g., methyl, ethyl, isopropyl, tert.-butyl, and the like, and may be substituted with one or more of a variety of substituents, such as halogen or hydroxyl.

When Y is an alkanoyl group in the above formula, it can be either straight or branched chain, e.g., be substituted with one or more substituents such as halogen or hydroxyl. When Y is aryloxy, it can be any such group having from 6 to 12 carbon atoms, such as benzyloyl. When Y represents a cation in the formula, it is preferably an ammonium radical, an alkaline metal cation, or an alkaline earth metal cation, but it can be any other agriculturally acceptable cation.

Preferred compounds coming within the scope of the above formula include, but are not limited to;

2-[1-(ethoxyimino)-butyl]-5-[2-(ethylthio)-propyl]-3-hydroxy-2-cyclohexene-1-one;

2-[1-(propoxyimino)-butyl]-5-[2-(ethylthio)-propyl]-3-hydroxy-2-cyclohexene-1-one;

2-[1(butoxyimino)-butyl]-5-[2-(propylthio)-propyl]-3-hydroxy-2-cyclohexene-1-one;

2-[1-(ethoxyimino)-pentyl]-5-[2-(propylthio)-butyl]-3-hydroxy-2-cyclohexene-1-one;

2-[1-(propoxyimino)-hexyl]-5-[2-(ethylthio)-pentyl]-3-hydroxy-2-cyclohexene-1-one;

2-[1-(ethoxyimino)-pentyl]-5-[2-(butylthio)-pentyl]-3-hydroxy-2-cyclohexene-1-one;

2-[1-(ethoxyimino)-butyl]-5-[2-(ethylthio)-propyl]-3-ethylcarbonyloxy-2-cyclohexene-1-one;

2-[1-(ethoxyimino)-butyl]-5-[2-(ethylthio)-propyl]-3-butylcarbonyloxy-2-cyclohexene-1-one, and the like.

The 2-alkoxyiminoalkyl-5-alkylthioalkyl-3-hydroxy-2-cyclohexene-1-one compounds or enol derivatives thereof are known compounds or can be prepared by conventional synthesis methods known to those skilled in the art. For example, 2-[1-(ethoxyimino)-butyl]-5-[2-(ethylthio)-propyl]-3-hydroxy-2-cyclohexene-1-one is a known compound and is available from the BASF Wyandotte Corporation of Parsippany, New Jersey as an experimental herbicide against a variety of annual and perennial grasses. Its preparation and use are disclosed in South African Pat No. 78/2404.

The compounds employed as plant sugar enhancers in the method of this invention are applied to the plant from 1 to 7 weeks prior to harvesting, preferably from 3 to 5 weeks prior to harvesting. Such compounds should be applied in an amount sufficient to increase the sugar content of the plant, i.e., an effective amount should be employed. As mentioned hereinbefore, however, the amount employed should be insufficient to exert a herbicidal effect on the plant. The proper amount is determined by and dependent upon such factors as the particular compound employed, the method of application, the particular plant species, the state and condition of growth of the plant, and the climatic conditions. Generally, from about ⅛ lb./acre to about 2 lbs./acre, preferably from about ¼ lb./acre to about 1 lb./acre, are employed.

The 2-alkoxyiminoalkyl-5-alkylthioalkyl-3-hydroxy-2-cyclohexene-1-ones employed in the method of this invention can be applied to mature plants in any suitable form, e.g., as solutions, emulsions, suspensions, dust formulations, and the like. Such compositions generally contain the active compound in an amount of from about 0.06 percent by weight to about 26 percent by weight, preferably from about 0.6 percent by weight to about 1.2 percent by weight. Both liquid compositions and dust formulations may be conveniently applied from either a ground rig or from an aircraft.

The preferred carrier for the active compounds employed in the method of this invention is water. When the active compound is water-soluble, it can be simply dissolved in an amount of water sufficient to give the desired concentration and sprayed on the plants. If desired, a suitable wetting agent may be added to the solution to improve wetting of the foliage and to increase the penetration of the solution into the tissue of the plant. Preferred wetting agents include anionic or nonionic surfactants such as sodium alkylsulfates, sodium alkylbenzenesulfonates, sodium ligninsulfonates, polyoxyethylene lauryl ethers, polyoxyethylene alkylaryl ethers, polyoxyethylene fatty acid esters, and polyoxyethylene sorbitan fatty acid esters. Such wetting agents generally do not exceed 1 percent by volume of the final spray solution, and preferably comprise about 0.1 percent to about 0.5 percent of the final spray volume.

Those active compounds which are not sufficiently water-soluble for conventional formulation into aqueous solutions can be prepared as liquid emulsions by dissolving the compounds in a small amount of an agriculturally acceptable solvent and then adding an emulsifier and water. Suitable solvents include n-hexane, toluene, xylene, naphtha, isophorone, dimethylformamide, and the like. Hydrocarbon oils, including paraffin oils, aromatic oils and asphaltic oils, can also be employed, although highly-aromatic oils are preferred, particularly highly-aromatic petroleum-base oils. Suitable emulsifiers include sodium ligninsulfonate, sodium 2,2'-dinaphthylmethane-6,6'-disulfonate, sodium dibutylsulfonate, and sodium oleylmethyllaurate.

Alternatively, these compounds may be formulated into wettable powders which can be dispersed in water by compounding them with conventional excipients such as fillers, wetting agents, dispersing agents, and the like. The wetting agents and emulsifiers mentioned above can be employed in this application. Suitable fillers include vermiculite, attaclay, talc, diatomaceous earth, pyrophillite, kaolin, bentonite and the like.

If desired, the active compounds employed in the method of this invention can be compounded with finely-divided, solid excipients, such as those named above, and applied to the plants as a dust formulation.

If desired, two or more active compounds can be employed in the method of the present invention. Should an admixture be employed, there is no prescribed ratio in which each particular compound must be present. The concentration of the admixture need only be within the concentration range of active material prescribed herein, and the rate of application of the admixture should be within the effective range prescribed herein.

The following examples are set forth for purposes of illustration so that those skilled in the art may better understand the invention. It should be understood, however, that they are exemplary only, and should not be construed as limiting this invention any any manner.

EXAMPLE 1

A twenty percent by weight emulsifiable concentrate of 2-[1-(ethoxyimino)-butyl]-5-[2-(ethylthio)-propyl]-3-hydroxy-2-cyclohexene-1-one in and an eighty-five percent by weight water soluble powder of a commercial sugarcane ripener, (N,N-bis(phosphonomethyl) glycine, sold by Monsanto Agricultural Products Company under the trade name Polaris were applied to 102 day old juvenile sugarcane plants (variety cp 65-357) and placed in the greenhouse. All treatments were applied in a volume equivalent to 100 gallons per acre. The composition of this invention was applied at the rate of ⅛, ¼, and ½ pounds per acre. Polaris was applied at a rate of 4 pounds per acre. There are five (5) applications for each treatment including an untreated control. Two weeks after treatment each plant was analyzed for total sugars by means of a refractometer and for reducing sugars using Benedict's cooper reduction reaction.

The average results for percent total sugars and reducing sugars obtained for each treatment are set forth in Table I below:

TABLE I

| Compound | Rate Lbs./Acre | Percent Total Sugars | Percent Reducing Sugars |
|---|---|---|---|
| Example I | ⅛ | 9.3 | 0.30 |
|  | ¼ | 10.2 | 0.25 |
|  | ½ | 10.2 | 0.25 |
| Polaris | 4 | 8.5 | 1.0 |
| Control | — | 7.4 | 1.2 |

Values for percent increase in total sugars and percent decrease in reducing sugars are set forth in Table II below:

TABLE II

| Compound | Rate Lbs./Acre | Percent Increase in Total Sugars | Percent Decrease in Reducing Sugars |
|---|---|---|---|
| Example 1 | ⅛ | 26 | 75 |
|  | ¼ | 38 | 79 |
|  | ½ | 38 | 79 |
| Polaris | 4 | 15 | 17 |

Although the invention has been illustrated by the preceding Example it is not to be construed as being limited to the compounds employed therein, but rather, the invention encompasses the generic area as hereinbefore disclosed. Various modifications and embodiments thereof can be made without departing from the spirit and scope thereof.

What is claimed is:

1. A method for increasing the sugar content of sugarcane or sorghum plants which comprises applying to such plants from 1 to 7 weeks prior to harvesting an effective amount of a compound of the formula

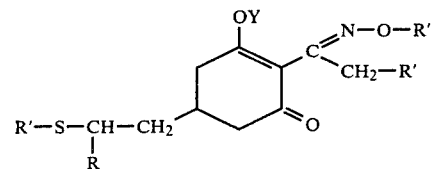

wherein:
R is an alkyl group having from 1 to 4 carbon atoms;
R' is an alkyl group having from 2 to 4 carbon atoms, and
Y is a hydrogen atom or an alkanoyl group having up to 12 carbon atoms.

2. A method as in claim 1 wherein application is made at a rate of from ⅛ lb./acre to 2 lbs./acre.

3. A method as in claim 1 wherein application is made at a rate of from ¼ lb./acre to 1 lb./acre.

4. A method as in claim 1 wherein the plants are sugarcane plants.

5. A method as in claim 4 wherein application is made at a rate of from ⅛ lb./acre to 2 lbs./acre.

6. A method as in claim 4 wherein application is made at a rate of from ¼ lb./acre to 1 lb./acre.

7. A method as in claim 4 wherein the compound is 2-[1-(ethoxyimino)-butyl]-5-[2-(ethylthio)-propyl]-3-hydroxy-2-cyclohexene-1-one.

8. A method as in claim 7 wherein application is made at a rate of from ⅛ lb./acre to 2 lbs./acre.

9. A method as in claim 7 wherein application is made at a rate of from ¼ lb./acre to 1 lb./acre.

10. A method as in claim 1 wherein the plants are sorghum plants.

11. A method as in claim 10 wherein application is made at a rate of from ⅛ lb./acre to 2 lbs./acre.

12. A method as in claim 10 wherein application is made at a rate of from ¼ lb./acre to 1 lb./acre.

13. A method as in claim 10 wherein the compound is 2-[1-(ethoxyimino)-butyl]-5-[2-ethylthio)-propyl]-3-hydroxy-2-cyclohexene-1-one.

14. A method as in claim 13 wherein application is made at a rate of from ⅛ lb./acre to 2 lbs./acre.

15. A method as in claim 13 wherein application is made at a rate of from ¼ lb./acre to 1 lb./acre.

16. A method as in claim 1 wherein application is made from 3 to 5 weeks prior to harvesting.

17. A method as in claim 16 wherein application is made at a rate of from ⅛ lb./acre to 2 lbs./acre.

18. A method as in claim 16 wherein application is made at a rate of from ¼ lb./acre to 1 lb./acre.

19. A method as in claim 16 wherein the compound is 2-[1-(ethoxyimino)-butyl]-5-[2-(ethylthio)-propyl]-3-hydroxy-2-cyclohexene-1-one.

20. A method as in claim 19 wherein application is made at a rate of from ⅛ lb./acre to 2 lbs./acre.

21. A method as in claim 19 wherein application is made at a rate of from ¼ lb./acre to 1 lb./acre.

22. A method as in claim 16 wherein the plants are sugarcane plants.

23. A method as in claim 22 wherein application is made at a rate of from ⅛ lb./acre to 2 lbs./acre.

24. A method as in claim 22 wherein application is made at a rate of from ¼ lb./acre to 1 lb./acre.

25. A method as in claim 22 wherein the compound is 2-[1-(ethoxyimino)-butyl]-5-[2-(ethylthio)-propyl]-3-hydroxy-2-cyclohexene-1-one.

26. A method as in claim 25 wherein application is made at a rate of from ⅛ lb./acre to 2 lbs./acre.

27. A method as in claim 25 wherein application is made at a rate of from ¼ lb./acre to 1 lb./acre.

28. A method as in claim 16 wherein the plants are sorghum plants.

29. A method as in claim 28 wherein application is made at a rate of from ⅛ lb./acre to 2 lbs./acre.

30. A method as in claim 28 wherein application is made at a rate of from ¼ lb./acre to 1 lb./acre.

31. A method as in claim 28 wherein the compound is 2-[1-(ethoxyimino)-butyl]-5-[2-(ethylthio)-propyl]-3-hydroxy-2-cyclohexene-1-one.

32. A method as in claim 31 wherein application is made at a rate of from ⅛ lb./acre to 2 lbs./acre.

33. A method as in claim 31 wherein application is made at a rate of from ¼ lb./acre to 1 lb./acre.

* * * * *